United States Patent [19]

Hairston

[11] 4,239,919

[45] Dec. 16, 1980

[54] PROCESS FOR OBTAINING BISPHENOLS

[75] Inventor: Thomas J. Hairston, Lake Jackson, Tex.

[73] Assignee: The Dow Chemical Company, Midland, Mich.

[21] Appl. No.: 47,854

[22] Filed: Jun. 12, 1979

[51] Int. Cl.$^3$ ............................................ C07C 39/12
[52] U.S. Cl. .................................... 568/727; 568/723
[58] Field of Search ................................ 568/727, 723

[56]  References Cited

U.S. PATENT DOCUMENTS

| 2,858,343 | 10/1958 | Hoaglin et al. | 568/723 |
| 2,884,462 | 8/1959 | Henry | 568/723 |

FOREIGN PATENT DOCUMENTS

| 63984/73 | 7/1975 | Australia | 568/727 |
| 1575847 | 7/1969 | France | 568/727 |

*Primary Examiner*—Paul J. Killos
*Attorney, Agent, or Firm*—A. C. Ancona

[57]  ABSTRACT

An improved process for obtaining bisphenols by reaction of a phenol, or substituted phenol having a hydrogen in the para position, and an alkenyl ether, wherein the unsaturation in the ether is in the alpha position, in the presence of a strong acid catalyst. The process gives particularly good results when bisisopropenyl ether is reacted with phenol in the presence of a strong acid cation exchange resin in which part of the exchange sites have been neutralized with 2,2-dimethylthiazolidine.

19 Claims, No Drawings

PROCESS FOR OBTAINING BISPHENOLS

Bisphenols have proven to be of considerable industrial importance. Particularly, the low molecular weight bisphenols obtained by condensing phenol with a ketone are important intermediates for the manufacture of epoxy, polyester, and modified phenolformaldehyde resins.

Methods of manufacturing bisphenols have changed over the years. Various conditions were employed in the beginning, e.g., the use of solvents, or diluents, and adjusting the temperature from room temperature to 90° C. A strong acid, such as concentrated HCl, was the condensing agent of choice although yields of less than 80% were obtained and products were impure.

In 1940, Perkins was awarded a patent (U.S. Pat. No. 2,191,831) on improvements utilizing anhydrous HCl, excess phenol, and controlled temperature. Yield was raised to 97% of theory, product purity reached 92%. The small reduction of water in the system was enough to effect much of the improved yield.

In 1944 Perkins and Bryner taught in U.S. Pat No. 2,359,242 that sulfur and ionizable sulfur compounds could be used to promote the condensation of phenols with ketones. This permitted carrying out the condensation at lower temperatures or more completely than before.

There were still problems with all the above methods. The soluble strong acid catalyst was difficult to remove as was the sulfur compound which also was objectionable because of its odorous nature. Yields were still limited. An equilibrium problem involving water, both that added with the reactants and present as a condensation product, limited yields.

Stoesser and Sommerfield taught in U.S. Pat. No. 2,623,908 an improved purification procedure involving the recovery of a crystallized product which was pure and odorless. As in previous processes, a certain amount of waste was generated in the recovery of excess phenol by distillation and a phenol-water azeotrope had to be dealt with.

With the advent of ion-exchange catalysis, as illustrated by U.S. Pat. No. 3,242,219, and the use of a "promoted" ion exchange resin as shown by U.S. Pat. Nos. 3,394,089 and 3,634,341, the presence of water became a more noticeable problem. Rates were slowed and conversions reduced. The strong acid cationic polymer exchange resins exhibited poor catalytic effects at water levels of more than one to two percent.

Mole ratios and feed rates of reactants across stationary catalyst beds become important in continuous systems to control water content. Recycle streams became larger because of the reduced conversions.

Reducing the water level in a phenol and acetone system would serve to shift the reaction equilibrium toward more product. This can be done mechanically by distillation, but is very costly. Here again, waste streams are produced consisting of water saturated with phenols.

Chemically reducing the water in a reactor or reactor stream would be most desirable. This would serve to eliminate azeotropes while also drying the system, thus increasing rates and yields. Certain unsaturated ethers have the ability of acting as water scavengers. In the phenol-acetone reaction to produce the bisphenol of acetone, bisisopropenylether (BIPE) is uniquely suited as a water scavenger because its reaction product with water is acetone, thus:

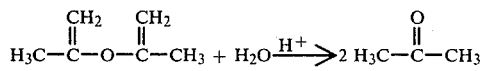

SUMMARY OF THE INVENTION

It has now been found that in the process of preparing a bisphenol from a ketone and a phenol having a reactive hydrogen substituted in the para position in the presence of a suitable strong acid catalyst and under the conditions of temperature and mole ratios known to the art, that the by-product water produced can be substantially decreased by replacing all or part of the ketone reactant with a reactive alkenyl ether wherein the olefinic unsaturation is in the alpha position with respect to the ether linkage.

Thus, for example, in the acetone-phenol reaction, by substituting BIPE for the acetone one can eliminate half the water in the product since one mole of water is used up in making acetone from the ether. Thus, instead of the normal acetone-phenol reaction, using 2 moles of phenol and one of acetone, to produce one mole of bisphenol and one mole of water in the product, thus:

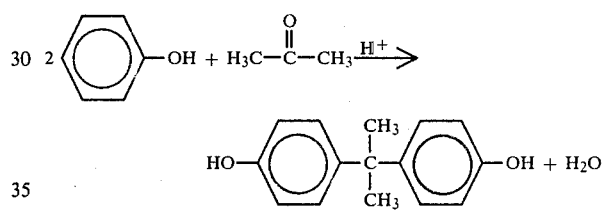

one employs twice the phenol with one mole of the ether to obtain two moles of bisphenol and the same amount of water in the product, thus:

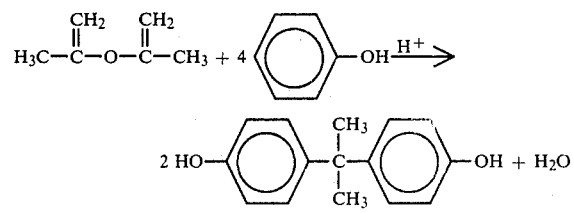

Bisisopropenyl ether can also be utilized in conjunction with acetone in varying amounts to control the water at any concentration desired.

DETAILED DESCRIPTION OF THE INVENTION

The improvement in the process for making bisphenols comprises the use of an alpha-unsaturated alkenyl ether as a substitute for all or a portion of the ketone in its reaction with a phenol in the presence of a suitable strong acid catalyst to make bisphenols. The alkenyl ether can be employed under substantially the same conditions as are known to the art for the reaction of a ketone and a phenol to make bisphenols.

Catalysts useful in the present invention are those suitable strong acids known to the art, including anhydrous HCl (U.S. Pat No. 2,191,831), mineral acids such as concentrated aqueous solutions of HCl and $H_2SO_4$ (U.S. Pat. No. 2,359,242), organic sulfonic acids, and the strong cation exchange resins (U.S. Pat. No. 3,242,219) in the acid form.

The promoters, i.e., the sulfur compounds used as additives, such as those used with soluble catalysts, e.g., methyl mercaptan, ethyl mercaptan, and octyl mercaptan, and those modified cation exchange resins which are partially neutralized with sulfur compounds including esters of sulfonic acids with mercapto alcohols, e.g., 1-hydroxy-2-mercaptoethane, and the partial salts of mercaptoethylamine and 2,2-diaminothiazolidine, are also useful in the practice of the present invention.

The temperatures employed are in the range of from about 45° C. to about 120° C., but preferably are maintained from about 45° C. to about 80° C. In a continuous system employing beds of cation exchange resin in the acid form, a feed rate of 1-6 bed volumes per hour is preferred, but as low as 0.2 or as high as 10 bed volumes per hour can be employed. This represents a contact time of from about 6 minutes to about 5 hours.

Any phenol, or substituted phenol, having a hydrogen in the para-position which can be substituted, i.e., active hydrogen, is operable in the process of the present invention. Thus, for example, phenol, ortho- and meta-cresol, 2,6-dimethylphenol, 2,6-dibromophenol, ortho- and meta-chlorophenol and ortho-phenylphenol and other substituted phenols containing alkyl, halogen or other groups, non-reactive under the conditions of the reaction, may be employed.

Alkenyl ethers which can be used in the reaction are those having the formula:

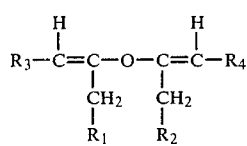

wherein $R_1$, $R_2$, $R_3$, and $R_4$ are independently selected from the group consisting of hydrogen, alkyl, cycloalkyl and aryl groups having from one to 10 carbon atoms. Specific examples of useful reactive alkenyl ethers are bisisopropenyl ether, bisisobutenyl ether, and isopropenylisobutenyl ether.

The following examples illustrate the process of the invention and the comparative examples show the advantages over and relationship to the prior art.

EXAMPLE 1.

Phenol-BIPE Reaction Using Ion Exchange Catalyst

A mixture of phenol and sulfonic acid cation exchange resin, (acetone-dried, nitrogen purged to remove acetone), in acid form (DOWEX 50WX4 resin, H+ form*, 4.08 meq/g dry resin) was brought to the desired run temperature in a 1000-ml stirred glass pot. BIPE was added dropwise over a period of time to control the reaction at the desired temperature. Stirring was continued and temperature maintained for a total time of 1¾ to 2 hours at which time the mixture was vacuum distilled to remove phenol, water, and unreacted acetone. The reaction was run at temperatures of 55° and 65° C. Runs 1 and 2 and comparative runs A and B were made using the same times and temperatures, but A and B employed an equivalent amount of acetone in place of the BIPE. Results are shown in Table I.

*2.2-Dimethylthiazolidine was employed to promote resin in the manner of U.S. Pat. No. 3,634,341; about 20% of the acid sites on the resin were neutralized.

TABLE I

| Run No. | 1 | A | 2 | B |
|---|---|---|---|---|
| Phenol (g) | 400 | 400** | 400 | 400 |
| Acetone (g) | 0 | 15** | 0 | 15 |
| BIPE (g) | 12.7** | 0 | 12.7 | 0 |
| Dowex 50WX4 (ml) | 70 | 70 | 70 | 70 |
| Temperature, °C. | 55 | 55 | 65 | 65 |
| Time (hrs.) | 1¾ | 1¾ | 2 | 2 |
| Product |  |  |  |  |
| % Acetone Conversion by stripping | 93.6 | 65.2 | 95.0 | 63.3 |
| % o,p-bisphenol A | 2.4 | 1.5 | 2.8 | 2.0 |
| % Bisphenol in Mixture | 13.3 | 9.27 | 13.5 | 9.0 |

**Phenol = 4.26 moles, acetone = 0.26 mole and BIPE = 0.13 mole.

EXAMPLE 2

Bisphenol Preparation Using a Soluble Sulfonic acid Catalyst

The reaction was run as in Example 1 except using a soluble catalyst. The same type comparison run as in Example 1 employing acetone (Run C) was also made. To a 1000-ml stirred glass pot containing 470 grams phenol and 16.7 grams BIPE was added 5.0 grams paratoluenesulfonic acid. The pot was heated at 75° C. until the reaction was completed (GC* analysis). A sample was neutralized with DOWEX 1 beads (basic form) and distilled under vacuum to remove phenol, water, and acetone. Results are shown in Table II.

*GC-Gas Chromatograph.

TABLE II

| Run No. | 3 | C |
|---|---|---|
| Phenol (g) | 470# | 470 |
| Acetone (g) | 0 | 19.6# |
| BIPE (g) | 16.7# | 0 |
| Paratoluene sulfonic acid (g) | 5.0 | 5.0 |
| % Bis A in Mixture | 11.5 | 8.8 |

Phenol = 5.0 moles, acetone = 0.34 mole, and BIPE = 0.17 mole.

The addition of BIPE to a reaction mixture of acetone and phenol in the presence of an acid catalyst will improve acetone conversion by acting as a water scavenger. The following experiment illustrates this:

EXAMPLE 3

BIPE Addition to Phenol-Acetone Reaction Mixture

A mixture of 400 grams (4.26 moles) of phenol, 20 grams (0.345 mole) of acetone, and 70 ml of phenolazeotrope-dried sulfonic acid cation exchange resin in acid form (DOWEX 50WX4 resin, H+ form, 4.08 meq/g dry resin) promoted as in Example 1 was brought to equilibrium in a stirred glass pot at 60° C. A 200-gram sample of liquid was removed from the pot. By distilling off excess phenol and water to final conditions of 200° C., 10 mm Hg vac, 7.25 grams of crystalline, light yellow solid was recovered from the distillation pot. This crystalline substance was identified as bisphenol A by elution time on the gel permeation chromatograph (GPC). To the remaining reaction mixture in the pot was added dropwise 17.3 grams (0.177 mole) of bisisopropenyl ether. The temperature rose from 60° to 65° C. The absence of water and rise of acetone was detected by gas chromatograph. After stopping the BIPE addition the temperature fell and water was detected by GC. From 180 grams of reaction mixture was recovered 36 grams of product by distilling off excess phenol and water under vacuum. The crystalline product was identified as bisphenol A by elution time on the GPC. The addition of BIPE raised acetone conversion from 19.4 to 58.2% of theoretical in this example of an ion exchange catalyzed stirred pot.

EXAMPLE 4

Continuous Process

The following experiments shows comparisons among preparations of bisphenol from phenol and acetone (Run D), from a mixture of acetone, BIPE and phenol (Run 4) and BIPE and phenol (Run 5), all in the presence of the catalyst of Example 1. All experiments were run in a small stainless steel continuous system using two consecutive reactors.

The phenol feed rate was approximately ten pounds per hour. The reaction temperature was maintained between 50° and 70° C. Acetone was mixed with the phenol and both were fed together into the system.

BIPE was fed into the top of the first reactor in Run 4 and into the tops of both reactors in Run 5. Results are shown in Table III.

TABLE III

| Run No. | 4 | 5 | D |
| --- | --- | --- | --- |
| % Acetone | 3.0 | 0 | 4 |
| % BIPE | 2.2 | 2.2 | 0 |
| % Bis A in Stream | 16.0 | 9.5 | 11.8 |
| % o,p-Bis A | 2.9 | 2.7 | 2.2 |
| % Conversion | 68 | 89 | 75 |

NOTE: 2.2% BIPE equivalent to 2.7% Acetone.

We claim:

1. The process for preparing a bisphenol which comprises reacting a phenol, or substituted phenol, having a reactive hydrogen in the para-position on the aromatic ring, with a reactive bis alkenyl ether, wherein the olefinic unsaturation is in the alpha position with respect to the ether linkage, in the presence of a suitable strong acid catalyst, and wherein the reaction temperature is maintained within the range of from about 45° to about 120° C. for a period of time of from about 6 to about 300 minutes.

2. The process of claim 1 in which the catalyst is a soluble aromatic sulfonic acid.

3. The process of claim 1 in which the catalyst is a strong acid cation exchange resin in the acid form.

4. The process of claim 1 wherein the reaction is promoted with a sulfur compound.

5. The process of claim 2 wherein the acid catalyst is p-toluene sulfonic acid.

6. The process of claim 4 wherein the catalyst is a cation exchange resin in the acid form in which a portion of the acid sites have been neutralized with a dialkylthiazolidine.

7. The process of claim 6 wherein the dialkylthiazolidine is dimethylthiazolidine.

8. The process of claim 7 wherein the dimethylthiazolidine is employed to neutralize about 20% of the acid sites of the cation exchange resin.

9. The process of claim 7 wherein the phenol is phenol.

10. The process of claim 9 wherein the alkenyl ether is bisisopropenyl ether.

11. In the process of making a bisphenol by reacting a phenol, or substituted phenol, having a reactive hydrogen in the para-position on the aromatic ring, with a ketone in the presence of a suitable strong acid catalyst, the improvement which comprises adding to the reaction mixture a reactive alkenyl ether as a water scavenger, and wherein the reaction temperature is maintained within the range of from about 45° to about 120° C. for a period of time of from about 6 to about 300 minutes.

12. The process of claim 11 in which the ether is a bis-alkenyl ether.

13. The process of claim 12 in which the bis-alkenyl ether, upon hydrolysis will produce the ketone reactant of the process.

14. The process of claim 12 in which the phenol is phenol.

15. The process of claim 14 wherein the ketone is acetone.

16. The process of claim 11 wherein the acid catalyst is a cation exchange resin in the acid form.

17. The process of claim 11 wherein part of the acid sites of the cation exchange resin have been neutralized with a dialkylthiazolidine.

18. The process of claim 15 wherein the dialkylthiazolidine is dimethylthiazolidine.

19. The process of claim 16 wherein the dimethylthiazolidine is employed to neutralize about 20% of the acid sites of the cation exchange resin.

* * * * *